(12) United States Patent
Toth

(10) Patent No.: US 7,620,142 B1
(45) Date of Patent: Nov. 17, 2009

(54) METHOD AND APPARATUS FOR REDUCING X-RAY DOSAGE IN CT IMAGING PRESCRIPTION

(75) Inventor: Thomas L. Toth, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 444 days.

(21) Appl. No.: 11/275,698

(22) Filed: Jan. 25, 2006

Related U.S. Application Data

(63) Continuation of application No. 10/063,373, filed on Apr. 16, 2002, now Pat. No. 7,254,623.

(51) Int. Cl.
*H05G 1/46* (2006.01)

(52) U.S. Cl. ............... 378/16; 378/108; 378/109; 378/110; 378/111; 378/112; 378/115; 378/116; 378/117; 600/407; 600/425

(58) Field of Classification Search ............ 378/16, 378/108, 109, 110, 111, 112, 115, 116, 117; 600/407, 425
See application file for complete search history.

(56) References Cited

U.S. PATENT DOCUMENTS

| | | | |
|---|---|---|---|
| 4,739,480 A | | 4/1988 | Oono et al. |
| 5,671,359 A | | 9/1997 | Godlewski et al. |
| 6,094,468 A | * | 7/2000 | Wilting et al. ............ 378/8 |
| 6,201,249 B1 | | 3/2001 | Yamayoshi |
| 6,205,198 B1 | | 3/2001 | Garland et al. |
| 6,272,469 B1 | * | 8/2001 | Koritzinsky et al. ...... 705/2 |
| 6,272,481 B1 | | 8/2001 | Lawrence et al. |
| 6,408,043 B1 | | 6/2002 | Hu et al. |
| 6,415,295 B1 | | 7/2002 | Feinberg |

(Continued)

FOREIGN PATENT DOCUMENTS

JP 62-092660 A 4/1987

(Continued)

OTHER PUBLICATIONS

Kalendar et al., A PC Program for Estimating Organ Dose and Effective Dose Values in Computed Tomography, European Radiology, 1999, vol. 9, No. 3, pp. 555-562 Germany.

(Continued)

*Primary Examiner*—Allen C. Ho
(74) *Attorney, Agent, or Firm*—Ziolkowski Patent Solutions Group, SC

(57) ABSTRACT

The present invention is directed to a networked scanner environment wherein each scanner is communicatable with one or more databases configured to store data associated with previously executed imaging sessions. The one or more databases may be queried by a user to determine, based on a set of user inputs, an historical evaluation of the prior imaging sessions conducted in accordance with scan parameters similar to the scan parameters of an imminent imaging session. The present invention includes a global database that is accessible by a series of remotely located imaging systems as well as includes one or more databases particular to a specific treatment facility housing one or more imaging scanners. The present invention is also applicable with a stand-alone imaging system having a database local to that particular imaging system for storing and accessing data associated with imaging sessions conducted on that particular imaging system.

20 Claims, 5 Drawing Sheets

U.S. PATENT DOCUMENTS

| | | | |
|---|---|---|---|
| 6,430,428 B1 | 8/2002 | Lindstedt | |
| 6,498,486 B1 | 12/2002 | Ookawa | |
| 6,597,938 B2 | 7/2003 | Liu | |
| 6,611,846 B1 | 8/2003 | Stoodley | |
| 6,668,184 B1 | 12/2003 | Kleiman | |
| 6,690,961 B1 | 2/2004 | Kaufman et al. | |
| 6,694,335 B1 | 2/2004 | Hopmann et al. | |
| 6,768,982 B1 | 7/2004 | Collins et al. | |
| 6,845,261 B2 | 1/2005 | Pattersson et al. | |
| 6,859,513 B2* | 2/2005 | Sako | 378/16 |
| 6,901,277 B2* | 5/2005 | Kaufman et al. | 600/407 |
| 6,901,282 B2 | 5/2005 | Edelman | |
| 6,915,297 B2 | 7/2005 | Chou | |
| 6,927,576 B2 | 8/2005 | Hoshino | |
| 6,954,513 B2* | 10/2005 | Horiuchi | 378/4 |
| 7,050,532 B2* | 5/2006 | Gohno | 378/8 |
| 2007/0053503 A1* | 3/2007 | Zelnik et al. | 378/205 |
| 2007/0109294 A1* | 5/2007 | Gotman et al. | 345/418 |
| 2008/0130972 A1* | 6/2008 | Miller et al. | 382/131 |

FOREIGN PATENT DOCUMENTS

| | | |
|---|---|---|
| JP | 03-039137 A | 2/1991 |
| JP | 05-212018 A | 8/1993 |
| JP | 1994090938 A | 5/1994 |
| JP | 07-023937 A | 1/1995 |

OTHER PUBLICATIONS

Nakagawa et al., Clinical Usefulness of the Management and Delivery of Radiation-Dose Distribution Images using the Internet, Radiation Medicine, Jul. 1998, vol. 16, No. 4, pp. 283-287, Japan.

Wade et al., CT Standard Protocols Are of Limited Value in Assessing Actual Patient Dose, The British Journal of Radiology, Nov. 1997, vol. 70, No. 839, pp. 1146-1151, England.

* cited by examiner

METHOD AND APPARATUS FOR REDUCING X-RAY DOSAGE IN CT IMAGING PRESCRIPTION

CROSS REFERENCE TO RELATED APPLICATIONS

The present application is continuation of and claims priority of U.S. Ser. No. 10/063,373 filed Apr. 16, 2002, now U.S. Pat. No. 7,254,623 issued Aug. 7, 2007, the disclosure of which is incorporated herein by reference.

BACKGROUND OF THE INVENTION

The present invention relates generally to prescribing diagnostic imaging sessions and, more particularly, to a method and apparatus for prescribing an imaging session based on scan parameters of previously executed imaging sessions.

Increasingly, diagnostic imaging systems are being used to non-invasively acquire diagnostic data of a subject such as a medical patient. For example, computer tomography, ultrasound, and magnetic resonance imaging systems are increasingly being used to acquire medical diagnostic data to enable medical personnel to diagnose a number of medical conditions. Furthermore, x-ray and other systems are increasingly being used by airport security personnel to inspect luggage and other packages for contraband, guns, knives, explosives, etc.

A number of protocols have been developed to assist personnel in prescribing an imaging session depending upon the diagnostic data sought and the modality of the imaging system being used to acquire that diagnostic data. Notwithstanding these highly sophisticated and developed protocols, it has been difficult to develop a protocol that provides the optimum scan parameters for each possible imaging condition. That is, a number of factors contribute to defining the imaging parameters for an imaging session. For example, in acquiring diagnostic data of a medical patient, factors such as the patient's age, height, weight, gender, data sought, and imaging system model must be considered. As a result, it is difficult for imaging personnel to prescribe imaging sessions consistently or prescribe sessions similar to that prescribed by other system operators. This concern is exacerbated when the imaging systems are located remotely from one another.

Additionally, it would be advantageous for imaging facilities to maintain up-to-date records of the parameters of each imaging session. For example, the x-ray dosage used to acquire computed tomography data of a medical patient may be useful records to maintain in order to track and minimize exposure.

Furthermore, patients and radiologists are increasingly expressing a desire to reduce or minimize the amount of radiation used to acquire imaging data. Therefore, there is certainly a need to monitor radiation dosage across CT systems and across treatment facilities to optimize the radiation dose exposure to the patient.

It would therefore be desirable to design a network and system of imaging systems that enables the evaluating of scan parameters of previously executed imaging sessions to determine the optimum scan parameters for an imminent imaging session.

BRIEF DESCRIPTION OF THE INVENTION

The present invention is directed to a method and apparatus for acquiring imaging data overcoming the aforementioned drawbacks. A networked scanner environment is provided wherein each scanner is communicatable with one or more databases configured to store data associated with previously executed imaging sessions. The one or more databases may be queried by a user to determine, based on a set of user inputs, an historical evaluation of the prior imaging sessions conducted in accordance with scan parameters similar to the scan parameters of an imminent imaging session. The present invention includes a global database that is accessible by a series of remotely located imaging systems as well as includes one or more databases particular to a specific treatment facility housing one or more imaging scanners. The present invention is also applicable with a stand-alone imaging system having a database local to that particular imaging system for storing and accessing data associated with imaging sessions conducted on that particular imaging system.

In accordance with one aspect of the present invention, an apparatus having a computer readable storage medium comprises an updatable database having data of one or more previous imaging scans stored therein. The apparatus further includes a computer programmed to receive a request to initialize an imaging scan from a user as well as receive input from the user identifying a desired imaging scan. The computer is further programmed to access the updatable database and compare data stored thereon of the one or more previous imaging scans with the desired imaging scan. The comparison is conveyed to the user for analysis.

In accordance with another aspect of the present invention, a method of constructing a network for administering imaging sessions includes the steps of providing at least one database for storing a plurality of scan parameter values. The method further includes the step of configuring an imaging scanner to be communicatable with the database and further configuring the imaging scanner to automatically transmit scan parameter values for a set of scan parameters to the at least one database following execution of an imaging scan. The method further includes the step of providing a user module connected to the imaging scanner and communicatable with the at least one database as well as configuring the user module to access the database in response to the user input to determine a summary of prior imaging scans.

In accordance with a further aspect of the present invention, an electronic network includes at least one updatable database configured to store scan parameter values from one or more imaging sessions and at least one imager configured to acquire imaging data of a subject. The network further includes an electronic communications link connected to the at least one updatable database and the at least one imager. The at least one imager includes a processor configured to automatically transmit one or more scan parameter values to the at least one updatable database following acquisition of imaging data from the subject.

In accordance with yet another aspect of the present invention, a computer readable storage medium having a computer program stored thereon is provided. The computer program represents a set of instructions that when executed by one or more computers causes the one or more computers to access a database having scan parameter data stored thereon wherein the scan parameter data correspond to scan parameters of one or more executed imaging sessions. The set of instructions further causes the one or more computers to compare user input identifying scan parameters of an imminent imaging session to at least a portion of the scan parameter data stored on the database. The one or more computers are further caused to determine preferred scan parameters for the imminent imaging session from the scan parameter data stored on the database from the one or more executed imaging sessions executed in accordance with scan parameters similar to those identified by the user input.

In accordance with yet a further aspect of the present invention, a method of prescribing an imaging session comprises the steps inputting a number of scan parameters of an imminent imaging session and comparing the number of scan parameters of the imminent imaging session to a number of scan parameters of one or more previously executed imaging sessions. The method further includes a step of allowing, based on the comparison, modification of radiation dosage for data acquisition for the imminent imaging session.

In accordance with yet another aspect of the present invention, a method of prescribing an imaging scan is provided. The method includes the steps of defining a proposed scan protocol and retrieving scan data from at least one similar scan prescription based on the proposed scan protocol. The method further includes the step of comparing dose exposure of the scan data with that of the proposed scan protocol. The method also includes the step of allowing adjustment to the proposed scan protocol to reduce dose exposure if the comparison results in excessive deviation.

In accordance with yet a further aspect of the present invention, a method of prescribing an imaging scan is provided. The method includes the steps of prescribing a scan to acquire imaging data of a subject and accessing at least one database having data stored thereon from executed scans. The method further includes a step of retrieving scan data from the database corresponding to executed scans similar to the prescribed scan. The prescribed scan is then executed with scan parameters defined by the scan data retrieved from the database.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Figure 1:
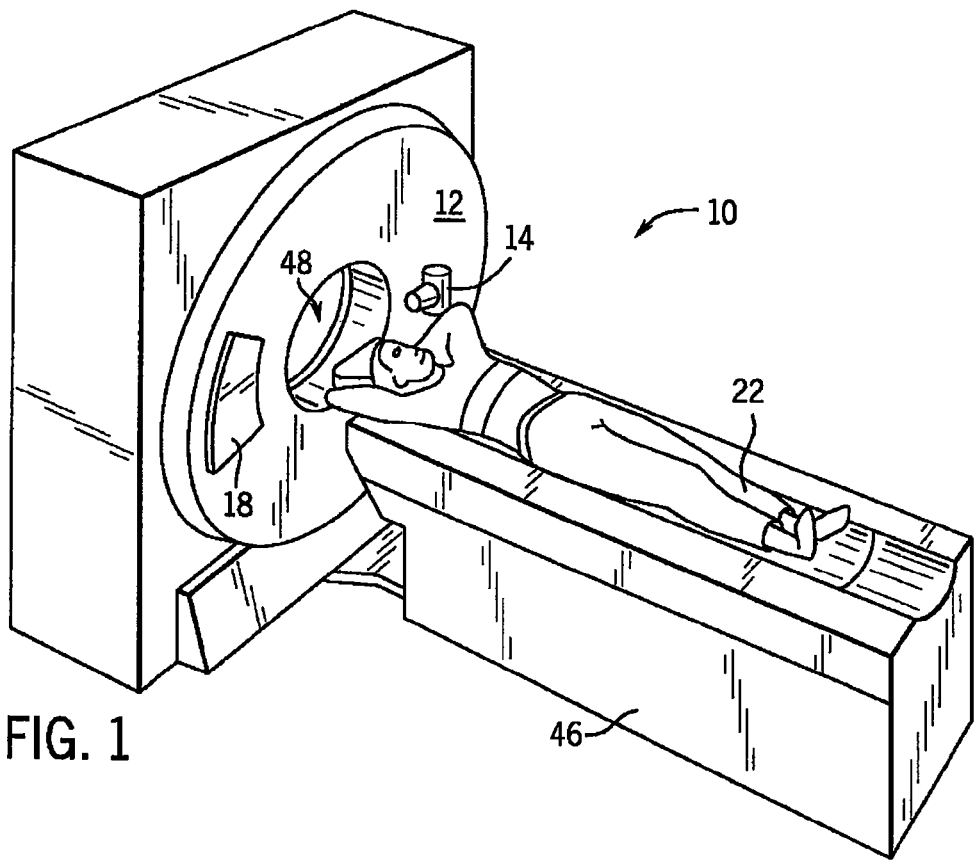
FIG. 1 is a pictorial view of a CT imaging system.
Figure 2:
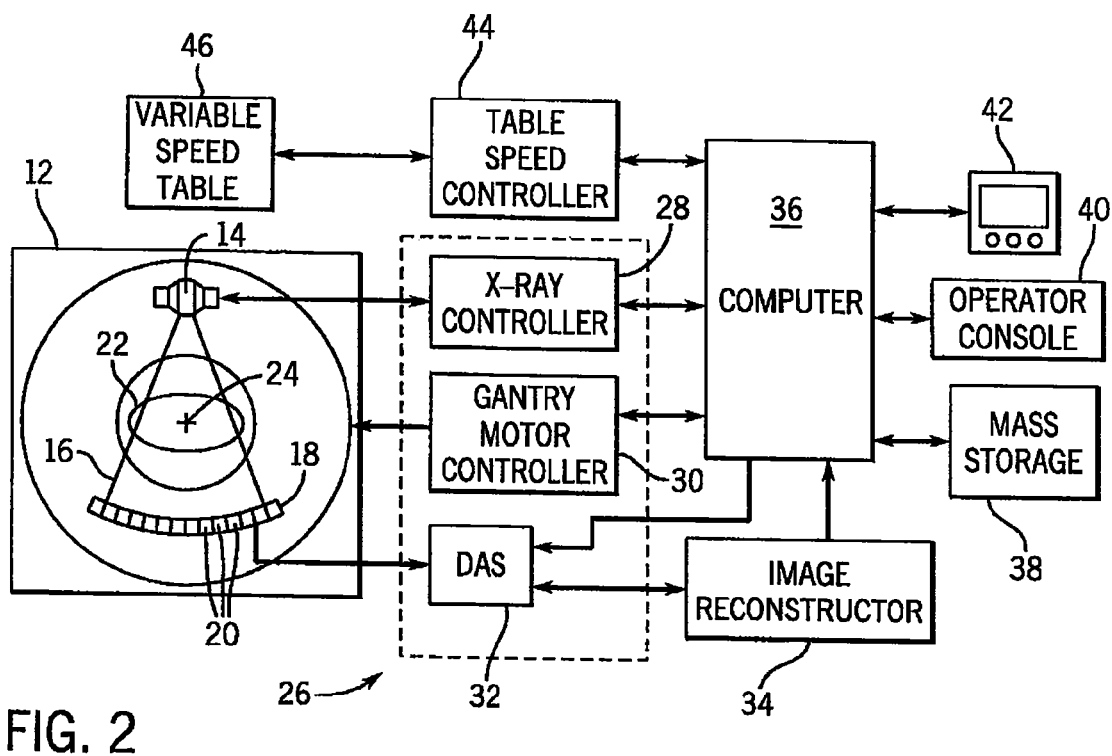
FIG. 2 is a block schematic diagram of the system illustrated in FIG. 1.

Referring to FIGS. 1 and 2, a "third generation" CT imaging system 10 is shown as including a gantry 12. The present invention, however, is applicable with other CT systems as well as other imaging modalities such as x-ray and magnetic resonance. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14, and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

Figure 3:
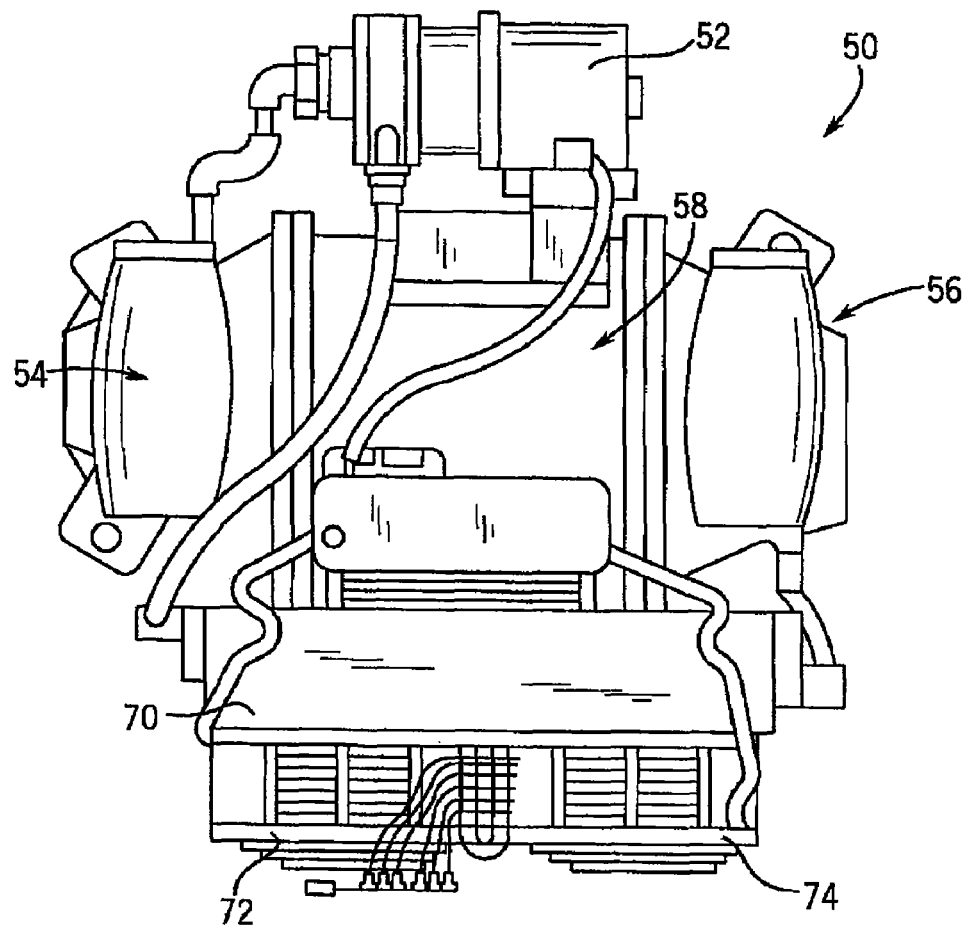
FIG. 3 is a plan view of a representative x-ray system.
Figure 4:
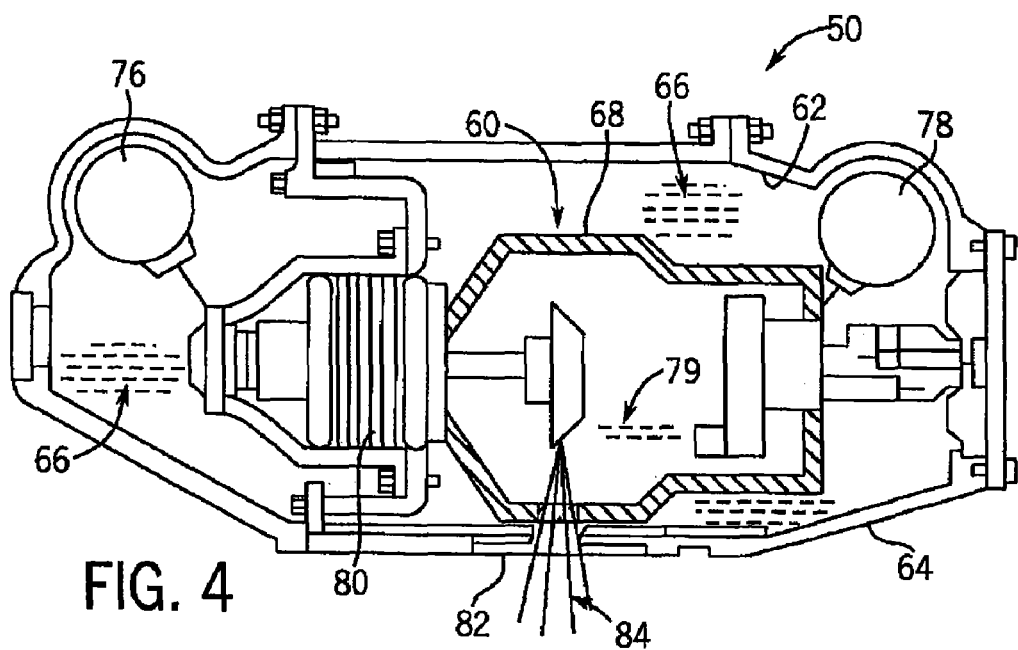
FIG. 4 is a sectional view of a portion of the x-ray system shown in FIG. 1.

Referring now to FIGS. 3-4, an x-ray system 50 incorporating the present invention is shown. The x-ray system 50 includes an oil pump 52, an anode end 54, and a cathode end 56. A central enclosure 58 is provided and positioned between the anode end 54 and the cathode end 56. Housed within the central enclosure 58 is an x-ray generating device or x-ray tube 60. A fluid chamber 62 is provided and housed within a lead lined casing 64. Fluid chamber 62 is typically filled with coolant 66 that will be used to dissipate heat within the x-ray generating device 60. Coolant 66 is typically a dielectric oil, but other coolants including air may be implemented. Oil pump 52 circulates the coolant through the x-ray system 50 to cool the x-ray generating device 60 and to insulate casing 64 from high electrical charges found within vacuum vessel 68. To cool the coolant to proper temperatures, a radiator 70 is provided and positioned at one side of the central enclosure 58. Additionally, fans 72, 74 may be mounted near the radiator 70 to provide cooling air flow over the radiator 70 as the dielectric oil circulates therethrough. Electrical connections are provided in anode receptacle 76 and cathode receptacle 78 that allow electrons 79 to flow through the x-ray system 50.

Casing 64 is typically formed of an aluminum-based material and lined with lead to prevent stray x-ray emissions. A stator 80 is also provided adjacent to vacuum vessel 68 and within the casing 64. A window 82 is provided that allows for x-ray emissions created within the system 50 to exit the system and be projected toward an object, such as, a medical patient for diagnostic imaging. Typically, window 82 is formed in casing 64. Casing 64 is designed such that most generated x-rays 84 are blocked from emission except through window 82.

Figure 5:
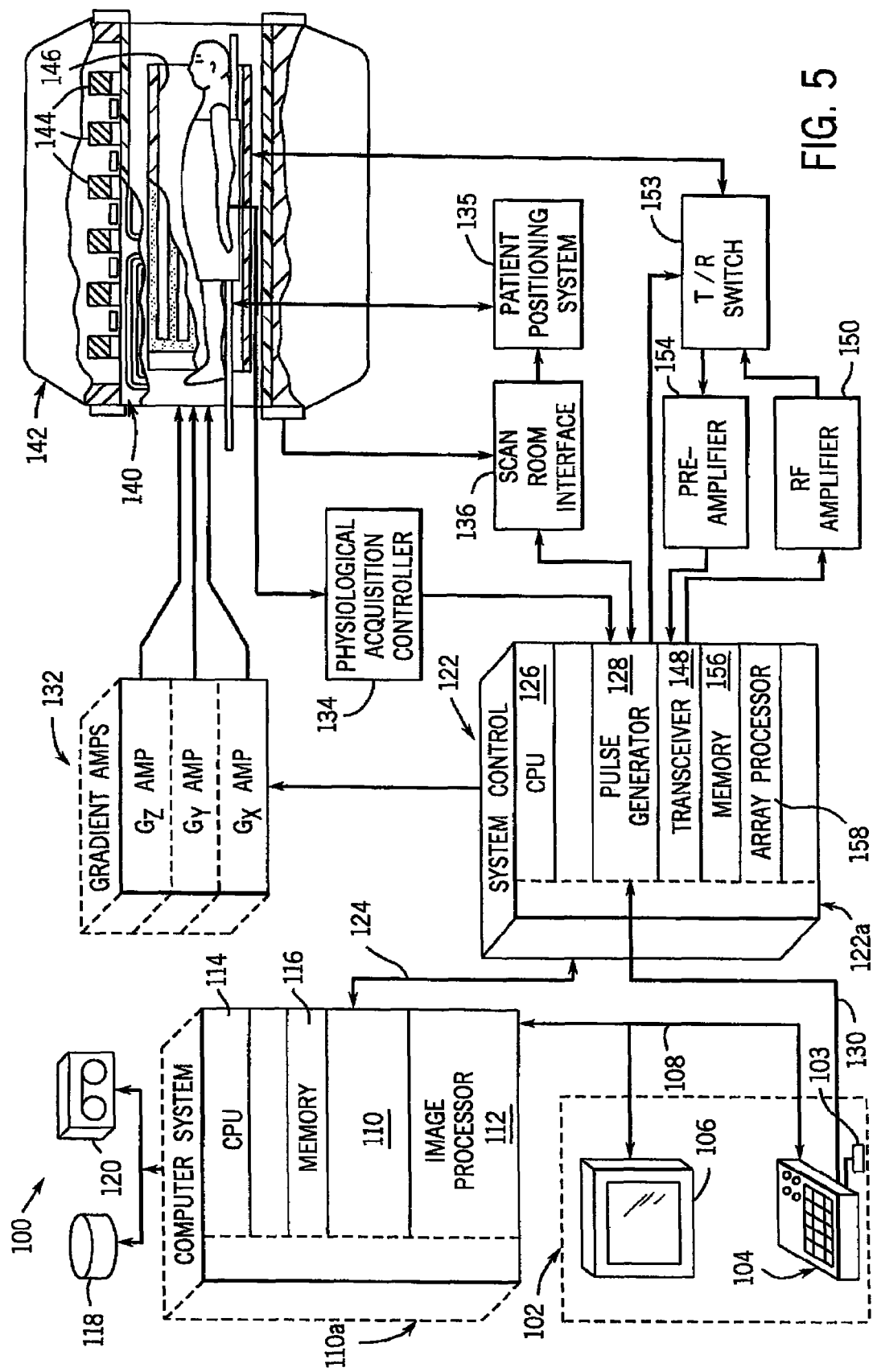
FIG. 5 is a schematic block diagram of an MR imaging system for use with the present invention.

Referring to FIG. 5, the major components of a preferred magnetic resonance imaging (MRI) system 100 incorporating the present invention are shown. The operation of the system is controlled from an operator console 102 which includes a keyboard or other input device 103, a control panel 104, and a display or screen 106. The console 102 communicates through a link 108 with a separate computer system 110 that enables an operator to control the production and display of images on the screen 106. The computer system 110 includes a number of modules which communicate with each other through a backplane 110a. These include an image processor module 112, a CPU module 114 and a memory module 116, known in the art as a frame buffer for storing image data arrays. The computer system 110 is linked to disk storage 118 and tape drive 120 for storage of image data and programs, and communicates with a separate system control 122 through a high speed serial link 124. The input device 103 can include a mouse, joystick, keyboard, track ball, touch activated screen, light wand, voice control, or any similar or equivalent input device, and may be used for interactive geometry prescription.

The system control 122 includes a set of modules connected together by a backplane 122a. These include a CPU module 126 and a pulse generator module 128 which connects to the operator console 102 through a serial link 130. It is through link 130 that the system control 122 receives commands from the operator to indicate the scan sequence that is to be performed. The pulse generator module 128 operates the system components to carry out the desired scan sequence and produces data which indicates the timing, strength and shape of the RF pulses produced, and the timing and length of the data acquisition window. The pulse generator module 128 connects to a set of gradient amplifiers 132, to indicate the timing and shape of the gradient pulses that are produced during the scan. The pulse generator module 128 can also receive patient data from a physiological acquisition controller 134 that receives signals from a number of different sensors connected to the patient, such as ECG signals from electrodes attached to the patient. And finally, the pulse generator module 128 connects to a scan room interface circuit 136 which receives signals from various sensors associated with the condition of the patient and the magnet system. It is also through the scan room interface circuit 136 that a patient positioning system 135 receives commands to move the patient to the desired position for the scan.

The gradient waveforms produced by the pulse generator module 128 are applied to the gradient amplifier system 132 having Gx, Gy, and Gz amplifiers. Each gradient amplifier excites a corresponding physical gradient coil in a gradient coil assembly generally designated 140 to produce the magnetic field gradients used for spatially encoding acquired signals. The gradient coil assembly 140 forms part of a magnet assembly 142 which includes a polarizing magnet 144 and a whole-body RF coil 146. A transceiver module 148 in the system control 122 produces pulses which are amplified by an RF amplifier 150 and coupled to the RF coil 146 by a transmit/receive switch 153. The resulting signals emitted by the excited nuclei in the patient may be sensed by the same RF coil 146 and coupled through the transmit/receive switch 153 to a preamplifier 154. The amplified MR signals are demodulated, filtered, and digitized in the receiver section of the transceiver 148. The transmit/receive switch 153 is controlled by a signal from the pulse generator module 128 to electrically connect the RF amplifier 150 to the coil 146 during the transmit mode and to connect the preamplifier 154 to the coil 146 during the receive mode. The transmit/receive switch 153 can also enable a separate RF coil (for example, a surface coil) to be used in either the transmit or receive mode.

The MR signals picked up by the RF coil 146 are digitized by the transceiver module 148 and transferred to a memory module 156 in the system control 122. A scan is complete when an array of raw k-space data has been acquired in the memory module 156. This raw k-space data is rearranged into separate k-space data arrays for each image to be reconstructed, and each of these is input to an array processor 158 which operates to Fourier transform the data into an array of image data. This image data is conveyed through the serial link 124 to the computer system 110 where it is stored in memory, such as disk storage 118. In response to commands received from the operator console 102, this image data may be archived in long term storage, such as on the tape drive 120, or it may be further processed by the image processor 112 and conveyed to the operator console 102 and presented on the display 106.

Figure 6:
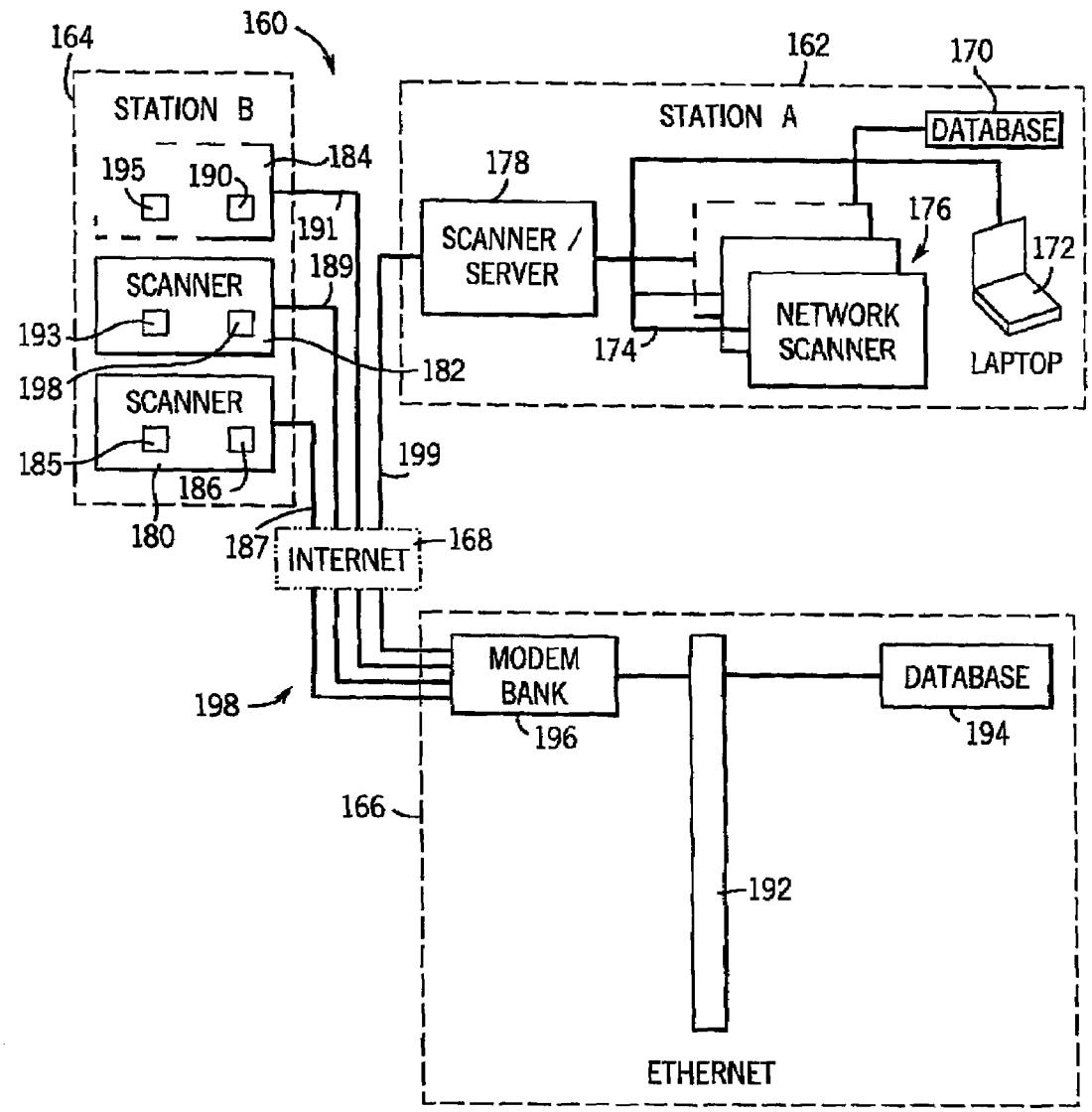
FIG. 6 is a schematic representation of one embodiment of the present invention.

Referring now to FIG. 6, an overview block diagram of a medical diagnostic and service networked system 160 is shown which includes a plurality of remote treatment stations, such as Station A referenced with numeral 162, and Station B referenced with numeral 164, which may include a medical treatment facility, hospital, clinic, or mobile imaging facility. It is understood, that the number of treatment stations can be limitless, but two specific embodiments are shown with Station A and Station B, which will be further explained hereinafter. The treatment stations 162, 164 are connected to a centralized facility 166 through a communications link, such as a network of interconnected server nodes 168. Although a single centralized facility is shown and described, it is understood that the present invention contemplates the use of multiple centralized facilities, each capable of communication with each treatment station. Each treatment station has operational software associated therewith which can be configured, serviced, maintained, upgraded, monitored, enabled or disabled by the centralized facility 166.

The various systems disclosed are configured to be selectively linked to the centralized facility 166 by a user module, which in the example of treatment station 162, includes a laptop computer 172 connected to an internal network 174. Such selective linking is desirable to provide upgrades, maintenance, service, and general monitoring of the various systems and equipment at a treatment site, which includes accessing data from the systems and transmitting data to the systems, for example.

In general, a treatment site may have a number of devices such as a variety of medical diagnostic systems of various modalities. As another example, in the present embodiment, the devices may include a number of networked medical image scanners 176 connected to an internal network 174 served by a single scanner 178 having a workstation configured to also act as a server, or configured as a stand-alone server without a medical image scanner associated therewith. Alternately, a treatment station or treatment site 164 can include a number of non-networked medical image scanners 180, 182, and 184 each having a computer or work station associated therewith and having an internal modem 186, 198, and 190 to connect the remote treatment station to a communications link, such as the Internet 168 through links 187, 189, and 191, respectively, to communicate with centralized facility 166. Internet 168 is shown in phantom to indicate that an external communications network can include Internet 168, together with communication links 199, 187, 189, and 191, or alternatively, can include direct dial-up links through dedicated lines, an intranet, or public communications systems.

It is understood that each of the network scanners 176 has its own workstation for individual operation and are linked together by the internal network 174. Additionally, each of the network scanners 176 is linked to a central database 170 configured to store data associated with imaging scan sessions, as will be discussed shortly. Further, such a system is provided with communications components allowing it to send and receive data over a communications link 199. Similarly, for the non-networked medical image scanners at remote treatment station 164, each of the scanners 180, 182, and 184 has individual communications links 187, 189, and 191 to the centralized facility 166. Furthermore, each scanner 180-184 may include a database 185, 193, 195, respectively, for storing scan parameter values. Although FIG. 6 shows each of these links connected through an open network 168, these links can permit data to be transferred to and from the systems over a dedicated network as well.

The embodiment shown in FIG. 6 contemplates a medical facility having such systems as magnetic resonance imaging (MRI) systems, ultrasound systems, x-ray systems, computed tomography (CT) systems, as well as positron emission tomography (PET) systems, or any other type of medical imaging system, however, the present invention is not so limited. Such facilities may also provide services to centralized medical diagnostic management systems, picture archiving and communications systems (PACS), teleradiology systems, etc. Such systems can be either stationary and located in a fixed place and available by a known network address, or be mobile having various network addresses. In the embodiment shown in FIG. 6, each treatment station 162, 164 can include any combination of the aforementioned systems, or a treatment station may have all of a single type of system. A treatment station can also include a single medical image scanner. Mobile diagnostic systems can be configured similarly to that of treatment station 162 or treatment station 164. Such mobile diagnostic systems can include equipment of various modalities, such as MRI, CT, ultrasound, or x-ray systems and are mobilized in order to service patients at various medical facilities. Each system is connectable and can transmit data through a network, such as an Ethernet 192 with one another, and/or with at least one database 194. However, it is understood that the single representation of a database 194 in FIG. 6 is for demonstrative purposes only, and it is assumed that there is a need for multiple databases in such a system. A bank of modems 196 is connected to the Ethernet 192 to relay data from the centralized facility 166 to the remote treatment stations 162, 164 through a plurality of modem links 198.

As previously discussed, each of the systems and substations described herein and referenced in FIG. 6 may be linked selectively to the centralized facility 166 via a network 168. According to the present invention, any acceptable network may be employed whether public, open, dedicated, private, or so forth. The communications links to the network may be of any acceptable type, including conventional telephone lines, fiber optics, cable modem links, digital subscriber lines, wireless data transfer systems, or the like. Each of the systems is provided with communications interface hardware and software of generally known design, permitting them to establish network links and exchange data with the centralized facility 166. The systems are provided with interactive software so as to configure the systems and exchange data between the customer stations and the centralized facility 166. In some cases, during periods when no data is exchanged between the customer stations and the centralized facility, the network connection can be terminated. In other cases, the network connection is maintained continuously.

Still referring to FIG. 6, in one preferred embodiment, database 194 located in the centralized facility 166 is configured to store data values associated with scan parameters of an imaging session for a particular imaging modality. For example, for a CT imaging system, the database may store scan parameter values associated with particular exam types such as head, face and sinuses, vertebral trauma, chest, lung, HRCT, abdomen, liver and spleen, pelvis, and osseous pelvis. Further, the scan parameter values stored on the database may also relate to certain demographic characteristics such as gender, age, and weight of the scan subject. These scan parameters assist in developing or choosing the appropriate dosage profile for acquiring CT data.

In one embodiment, the scan parameter values used to define an imaging scan session are automatically transmitted from the scanner to the database 194. That is, database 194 is automatically updated after each imaging scan is executed. Records must be maintained as to the dosage used and catalogued according to the particular diagnostic procedure as well as the individual patient. From these records, the treatment facilities or institutions may ensure conformity with dosage guidelines and regulations.

As a result of maintaining an active database storing scan parameter values of executed imaging sessions, a user or prescriber of an imminent imaging session may query the database to determine those scan parameters that are typically used to define an imaging session. For example, a CT technician or radiologist may define through a set of user inputs a number of scan parameters for an imminent scan session. Following definition of the imminent scan session, the user may then query database 194 to determine a mean radiation dosage, standard deviation, and optionally a histogram plot based on previously executed scan sessions executed in accordance with scan parameters similar to those defined by the set of user inputs. The database is queried to determine the mean dose, the standard deviation, and optionally the histogram plot by matching the scanner module, examination type, and patient demographic data identified by the set of user inputs with the values stored on the database. As a result, the prescriber of the imaging session may compare the anticipated dosage to acquire the imaging data to a statistical value of the dosage used in previously executed sessions conducted under similar conditions with similar equipment for similar patients. This allows the user to know prior to execution of an imaging session or prior to generation of a particular scan protocol how the anticipated dosage utilization compares to other imaging sessions. That is, if the user should find that the desired protocol dose is several standard deviations higher than the dose customarily used for similar scans as defined by the stored values on the database, it would serve as motivation to reconsider the prescribed dose protocol.

The present invention contemplates any queriable value being used to compare past imaging sessions to a particular imminent imaging session. For example, in the CT environment, not only may dosage be monitored or compared, but the user may also query the database to determine the noise index that is typically used by other network members for a particular clinical diagnostic objective or exam type.

As described above, the database having the scan parameter values stored thereon may be accessed from a number of scanners that are remotely located from the database. Furthermore, there is no requirement that each scanner be physically located in the same treatment station or facility. That is, a scanner located in station 162 may electronically transmit and receive data from database 194 while simultaneously therewith any scanner 180-184 in station 164 may likewise transmit and receive data to and from database 194. Furthermore, database 194 need not be located in a separate centralized facility 166. That is, database 194 may be located in either one of stations 162, 164 as well as be remotely located within that station or treatment facility from the various scanners. For example, Station A may include a database 170 electronically accessible by a number of network scanners 176 that automatically stores scan parameter values associated with particular scanning sessions. As such, database 170 may store those values associated with the imaging sessions executed within that particular treatment facility only. As a result, prior to an imaging session, the prescriber may compare the scan parameters of the imminent imaging session with the scan parameter values stored on database 170 corresponding to the imaging sessions conducted at that particular facility. This allows the user to locally compare the prescribed scan parameters to the scan parameters of previous imaging sessions conducted at that particular locality.

Notwithstanding the implementation of a local database, the network scanners 176 housed within Station A may also access a global database such as database 194 of centralized facility 166 for ascertaining historical data as to imaging sessions conducted by medical providers at differing treatment stations or treatment facilities. As a result, the session prescriber may not only determine a local pattern but also determine what others are doing with respect to imaging parameters for particular imaging sessions that are remotely located from his or her particular treatment facility.

The present invention also contemplates a scanner such as scanners 180-184 that are housed within a single treatment facility such as Station B wherein each scanner includes a database 185, 193, 195 configured to automatically store scan parameter values associated with scanning sessions executed on that particular scanner. This allows the session prescriber to compare the scan parameters for the imminent scan session to the scan parameters used to acquire imaging data during previous imaging sessions on that particular scanner. For example, the user may input a series of parameters for an imminent scanning session and then access the local database for that particular scanner to determine if the scan parameters for the imminent session coincide with the scan parameters typically used for similar imaging sessions. That is, the user may determine from the stored values on the scanner's local database if prior imaging sessions using that particular scanner for patients of similar size, weight, gender, and exam type are similar to the scan parameters the user defined for the imminent scan session.

As shown in FIG. 6, the present invention contemplates an embodiment in which a database is maintained at each level of the network system. For example, the network scanners 176 of Station A are not only connected to a local database 170 but may also access a global database 194 housed in a centralized facility 166. Moreover, the non-networked scanners 180-184 of Station B each include a local database 185, 193, 195 for storing scan parameter values of previously executed imaging sessions that may be accessible by a user to determine if the scan parameters defining an imminent scan session are similar to the scan parameters used in past imaging sessions as executed on that imaging system. It should be understood however that illustration of the non-network scanners as having the local databases does not preclude a networked scanner environment from utilizing a local database on each particular scanner. That is, a series of network scanners may each have a database local to that particular scanner as well as being electronically connected to a database for that particular treatment station as well as being electronically connected to a global database that may or may not be remotely located from that particular treatment facility.

Figure 7:
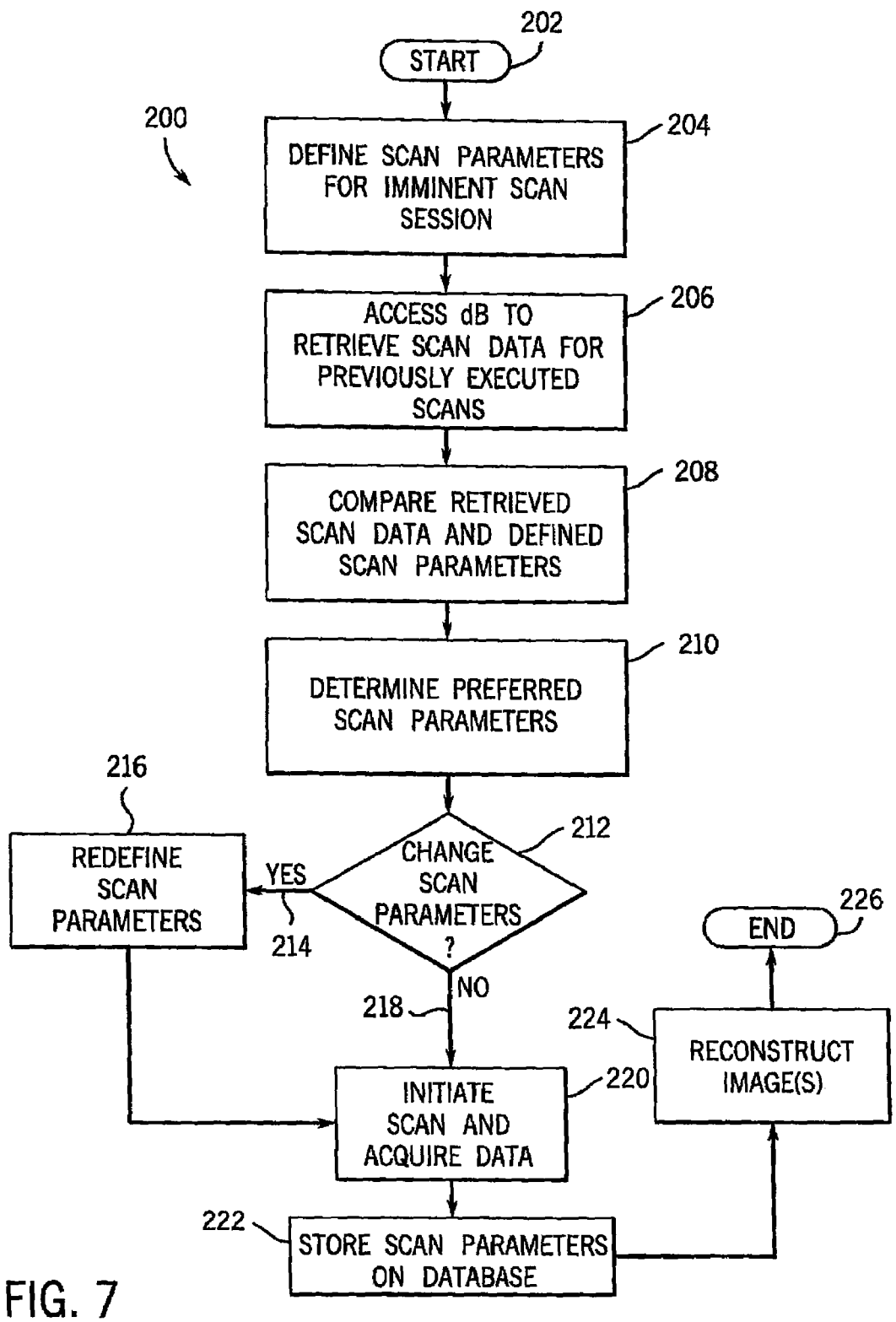
FIG. 7 is a flow chart for redefining scan parameters of an imminent imaging session in accordance with the present invention.

Referring now to FIG. 7, a process 200 for redefining scan parameters of an imminent imaging session based on scan parameters of previously executed imaging sessions will be described. The process begins at 202 with the defining of scan parameters for an imminent or proposed scan session 204. The scan parameters may include but are not limited to exam type, patient gender, patient age, and patient weight. Once the proposed scan is defined 204, the user may then access a database to retrieve scan data for previously executed scans at 206. As indicated previously, the database stores scan parameter data for previously executed scans which may be queried by a user to obtain historical information of executed exams having similar diagnostic objectives as the imminent proposed scan. For example, the user may access the database and obtain scan data relating to dosage used to obtain CT data during imaging sessions having scan parameters similar to those defined by the user at 204. The user may then compare the retrieved scan data with the previously defined scan parameters at 208 and thereby determine preferred scan parameters for the imminent scan based on previously executed but similar scan sessions 210.

At 212, the user may elect to change the scan parameters of the proposed imaging session. For example, the user may elect to redefine the scan parameters if the resulting radiation dosage to be projected toward the subject will exceed an allowable deviation. If the user elects to change the earlier defined scan parameters 212, 214, the user may do so at 216. However, if the user elects not to change the previously defined scan parameters 212, 218, the process continues with the initiation of the imaging scan and the acquisition of imaging data at 220. It should be noted, that once the user redefines the scan parameters at 216, the process also continues to scan initiation and data acquisition at 220.

Preferably, upon the acquisition of imaging data 220, the scan parameters defining the imaging session are automatically stored on the database at 222. By automatically storing the scan parameters, the process maintains an active database of current scan parameter data. At 224, images are reconstructed from the acquired imaging data according to known reconstruction techniques. The process then concludes at 226.

Alternately, a proposed scan may be prescribed at 204. The user may then access the database 206 to retrieve scan data for previously executed scans similar to the proposed scan at 204. Rather than comparing the retrieved scan data with scan parameters of the proposed or imminent scan session, the user may use the scan data acquired from the database to authoritatively define the scan parameters of the proposed scan. That is, the user initiates and conducts the scan based on scan data of previously executed scans at 220. In this embodiment, process 200 is simplified and may be particularly useful as a routine practice within a community hospital whereas process 200 in its entirety may be particularly useful for teaching or luminary institutions.

In accordance with one embodiment of the present invention, an apparatus having a computer readable storage medium comprises an updatable database having data of one or more previous imaging scans stored therein. The apparatus further includes a computer programmed to receive a request to initialize an imaging scan from a user as well as receive input from the user identifying a desired imaging scan. The computer is further programmed to access the updatable database and compare data stored thereon of the one or more previous imaging scans with the desired imaging scan. The comparison is conveyed to the user for analysis.

In accordance with another embodiment of the present invention, a method of constructing a network for administering imaging sessions includes the steps of providing at least one database for storing a plurality of scan parameter values. The method further includes the step of configuring an imaging scanner to be communicatable with the database and further configuring the imaging scanner to automatically transmit scan parameter values for a set of scan parameters to the at least one database following execution of an imaging scan. The method further includes the step of providing a user module connected to the imaging scanner and communicatable with the at least one database as well as configuring the user module to access the database in response to the user input to determine a summary of prior imaging scans.

In accordance with a further embodiment of the present invention, an electronic network includes at least one updatable database configured to store scan parameter values from one or more imaging sessions and at least one imager configured to acquire imaging data of a subject. The network further includes an electronic communications link connected to the at least one updatable database and the at least one imager. The at least one imager includes a processor configured to automatically transmit one or more scan parameter values to the at least one updatable database following acquisition of imaging data from the subject.

In accordance with yet another embodiment of the present invention, a computer readable storage medium having a computer program stored thereon is provided. The computer program represents a set of instructions that when executed by one or more computers causes the one or more computers to access a database having scan parameter data stored thereon wherein the scan parameter data correspond to scan parameters of one or more executed imaging sessions. The set of instructions further causes the one or more computers to compare user input identifying scan parameter of an imminent imaging session to at least a portion of the scan parameter data stored on the database. The one or more computers are further caused to determine preferred scan parameters for the imminent imaging session from the scan parameters data stored on the database from the one or more executed imaging sessions executed in accordance with scan parameters similar to those identified by the user input.

In accordance with yet a further embodiment of the present invention, a method of prescribing an imaging session comprises the steps inputting a number of scan parameters of an imminent imaging session and comparing the number of scan parameters of the imminent imaging session to a number of scan parameters of one or more previously executed imaging sessions. The method further includes a step of allowing, based on the comparison, modification of radiation dosage for data acquisition for the imminent imaging session.

In accordance with yet another embodiment of the present invention, a method of prescribing an imaging scan is provided. The method includes the steps of defining a proposed scan protocol and retrieving scan data from at least one similar scan prescription based on the proposed scan protocol. The method further includes the step of comparing dose exposure of the scan data with that of the proposed scan protocol. The method also includes the step of allowing adjustment to the proposed scan protocol to reduce dose exposure if the comparison results in excessive deviation.

In accordance with yet a further embodiment of the present invention, a method of prescribing an imaging scan is provided. The method includes the steps of prescribing a scan to acquire imaging data of a subject and accessing at least one database having data stored thereon from executed scans. The method further includes a step of retrieving scan data from the database corresponding to executed scans similar to the prescribed scan. The prescribed scan is then executed with scan parameters defined by the scan data retrieved from the database.

The present invention has been described in terms of the preferred embodiment, and it is recognized that equivalents, alternatives, and modifications, aside from those expressly stated, are possible and within the scope of the appending claims.

What is claimed is:

1. A method of prescribing an imaging session comprising the steps of:
   inputting a number of scan parameters of an imminent imaging session for an object to be scanned;
   comparing the number of scan parameters of the imminent imaging session to a number of scan parameters, stored in a database, of one or more previously executed imaging sessions of another object;
   determining how other prior users have conducted the one or more previously executed imaging sessions;
   modifying a radiation dosage of the imminent imaging session for data acquisition based on the determination;
   acquiring imaging data of the object using a protocol having the modified radiation dosage; and
   generating an image of the object using the imaging data for display.

2. The method of claim 1 further comprising the step of accessing the database having data stored thereon corresponding to the one or more previously executed imaging sessions.

3. The method of claim 2 further comprising the step of automatically storing the number of scan parameters and dosage used during execution of the imminent imaging session on the database.

4. The method of claim 1 further comprising the step of accessing the database via a communications link.

5. The method of claim 3 wherein the database is remotely located from a site of the imminent imaging session.

6. A method of prescribing an imaging scan comprising the steps of:
   defining a proposed scan protocol for imaging a patient;
   retrieving scan data from at least one similar scan prescription, conducted on other patients, based on the proposed scan protocol;
   comparing dose exposure of the scan data with that of the proposed scan protocol; and
   adjusting the proposed scan protocol to reduce dose exposure if excessive deviation results from the comparison;
   acquiring imaging data of the patient using the adjusted scan protocol; and
   transform the image data to an image of the patient using the acquired imaging data.

7. The method of claim 6 wherein the proposed scan protocol is based on at least one of an exam type, a demographics selection, a scanner model, and patient characteristics.

8. The method of claim 7 wherein:
   the exam type includes at least one of head, face and sinuses, vertebral trauma, chest, lung, heart, abdomen, liver, spleen, and pelvis;
   the demographics selection includes at least age, gender, age group, and weight group; and
   the patient characteristics include at least weight, age, and gender.

9. The method of claim 6 wherein the scan data is retrieved from one or more remotely located databases.

10. The method of claim 6 further comprising the step of prompting user-adjustment of at least one scan parameter if the comparison results in excessive deviation.

11. The method of claim 10 further comprising the step of re-determining predicted dose exposure following user adjustment to a scan parameter.

12. A CT system comprising:
   an x-ray source and an x-ray detector assembly operably connected to acquire CT data from an object; and a computer programmed to:
- receive a number of user-inputs indicative of parameters of an imminent scan;
- access a database and compare values for the number of user-inputs to stored values for the parameters used during execution of one or more executed scans;
- display results of the comparison to a user prior to execution of the imminent scan; and
- provide at least one of an audio and a visual indication if the comparison indicates that the imminent scan will have an unacceptable dose level.

13. The CT system of claim 12 wherein the computer is further programmed to receive a user-input modifying a parameter to reduce radiation dose in the imminent scan.

14. The CT system of claim 12 wherein the computer is further programmed to determine a predicted dose from the comparison.

15. The CT system of claim 12 wherein the computer is further programmed to automatically update the database after execution of the imminent scan.

16. The CT system of claim 12 wherein the computer, in being programmed to access the database, is programmed to access a database remotely located from the CT system.

17. The CT system of claim 16 wherein the computer is programmed to acquire the stored values from a portion of the database comprising data regarding more than one CT system remotely located from the CT system.

18. The CT system of claim 12 wherein the computer is further programmed to prompt a user to make dose reduction adjustments to parameters of the imminent scan in response to the at least one of the audio and the visual indication.

19. A method of prescribing an imaging scan comprising the steps of:
- defining a scan protocol based on at least one of an exam type, a demographics selection, a scanner model, patient characteristics;
- retrieving scan data from at least one similar scan prescription based on the scan protocol;
- comparing dose exposure of the scan data with that of the scan protocol and determine a deviation therebetween; and
- adjusting the scan protocol to reduce dose exposure if excessive deviation results, based on the comparison;
- acquiring image data using the adjusted scan protocol; and
- displaying an image of the acquired image data.

20. The method of claim 19 wherein the exam type includes at least one of head, face and sinuses, vertebral trauma, chest, lung, heart, abdomen, liver, spleen, and pelvis; the demographics selection includes at least age, gender, age group, and weight group; and the patient characteristics include at least weight, age, and gender.

* * * * *

UNITED STATES PATENT AND TRADEMARK OFFICE
CERTIFICATE OF CORRECTION

| | | |
|---|---|---|
| PATENT NO. | : 7,620,142 B1 | Page 1 of 1 |
| APPLICATION NO. | : 11/275698 | |
| DATED | : November 17, 2009 | |
| INVENTOR(S) | : Thomas L. Toth | |

It is certified that error appears in the above-identified patent and that said Letters Patent is hereby corrected as shown below:

Col. 12, line 28 (Claim 5), delete "claim 3" and substitute therefore -- claim 4 --.

Signed and Sealed this

Twenty-sixth Day of January, 2010

David J. Kappos
*Director of the United States Patent and Trademark Office*

UNITED STATES PATENT AND TRADEMARK OFFICE
CERTIFICATE OF CORRECTION

PATENT NO.        : 7,620,142 B1                                          Page 1 of 1
APPLICATION NO.   : 11/275698
DATED             : November 17, 2009
INVENTOR(S)       : Thomas L. Toth It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 501 days.

Signed and Sealed this

Twenty-sixth Day of October, 2010

David J. Kappos
*Director of the United States Patent and Trademark Office*